(12) United States Patent
Haddad et al.

(10) Patent No.: US 11,776,691 B2
(45) Date of Patent: Oct. 3, 2023

(54) MACHINE LEARNING BASED DEPOLARIZATION IDENTIFICATION AND ARRHYTHMIA LOCALIZATION VISUALIZATION

(71) Applicant: Medtronic, Inc., Minneapolis, MN (US)

(72) Inventors: Tarek D. Haddad, Minneapolis, MN (US); Niranjan Chakravarthy, Singapore (SG); Donald R. Musgrove, Minneapolis, MN (US); Andrew Radtke, Minneapolis, MN (US); Eduardo N. Warman, Maple Grove, MN (US); Rodolphe Katra, Blaine, MN (US); Lindsay A. Pedalty, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 558 days.

(21) Appl. No.: 16/845,996

(22) Filed: Apr. 10, 2020

(65) Prior Publication Data

US 2020/0357517 A1 Nov. 12, 2020

Related U.S. Application Data

(60) Provisional application No. 62/843,786, filed on May 6, 2019.

(51) Int. Cl.
*G16H 50/20* (2018.01)
*G06N 20/00* (2019.01)
(Continued)

(52) U.S. Cl.
CPC ............. *G16H 50/20* (2018.01); *A61B 5/076* (2013.01); *A61B 5/339* (2021.01); *A61B 5/349* (2021.01);
(Continued)

(58) Field of Classification Search
CPC .................................................. G06F 2218/16
See application file for complete search history.

(56) References Cited

U.S. PATENT DOCUMENTS

| 4,458,691 A | 7/1984 | Netravali |
| 6,212,428 B1 | 4/2001 | Hsu et al. |
| | (Continued) | |

FOREIGN PATENT DOCUMENTS

| CN | 108030488 A | 5/2018 |
| EP | 1218060 B1 | 7/2002 |
| | (Continued) | |

OTHER PUBLICATIONS

Advisory Action from U.S. Appl. No. 16/851,500, dated May 17, 2022, 6 pp.

(Continued)

*Primary Examiner* — Di Xiao
(74) *Attorney, Agent, or Firm* — Shumaker & Sieffert, P.A.

(57) ABSTRACT

Techniques that include applying machine learning models to episode data, including a cardiac electrogram, stored by a medical device are disclosed. In some examples, based on the application of one or more machine learning models to the episode data, processing circuitry derives, for each of a plurality of arrhythmia type classifications, class activation data indicating varying likelihoods of the classification over a period of time associated with the episode. The processing circuitry may display a graph of the varying likelihoods of the arrhythmia type classifications over the period of time. In some examples, processing circuitry may use arrhythmia type likelihoods and depolarization likelihoods to identify depolarizations, e.g., QRS complexes, during the episode.

23 Claims, 9 Drawing Sheets

(51) Int. Cl.
*G06N 5/04* (2023.01)
*A61B 5/07* (2006.01)
*A61B 5/00* (2006.01)
*A61B 5/339* (2021.01)
*A61B 5/349* (2021.01)

(52) U.S. Cl.
CPC ............... *A61B 5/686* (2013.01); *G06N 5/04* (2013.01); *G06N 20/00* (2019.01); *A61B 5/7267* (2013.01)

(56) References Cited

U.S. PATENT DOCUMENTS

| | | | |
|---|---|---|---|
| 6,308,094 B1 | 10/2001 | Shusterman et al. | |
| 6,594,523 B1 | 7/2003 | Levine | |
| 8,103,346 B2 | 1/2012 | Mass et al. | |
| 8,521,281 B2 | 8/2013 | Patel et al. | |
| 9,183,351 B2 | 11/2015 | Shusterman | |
| 9,483,529 B1 | 11/2016 | Pasoi et al. | |
| 9,585,590 B2 | 3/2017 | McNair | |
| 9,743,890 B2 | 8/2017 | Lord et al. | |
| 9,775,559 B2 | 10/2017 | Zhang et al. | |
| 10,463,269 B2 | 11/2019 | Boleyn et al. | |
| 10,744,334 B2 | 8/2020 | Perschbacher et al. | |
| 2002/0016550 A1 | 2/2002 | Sweeney et al. | |
| 2002/0123768 A1 | 9/2002 | Gilkerson et al. | |
| 2006/0247709 A1 | 11/2006 | Gottesman et al. | |
| 2009/0259269 A1* | 10/2009 | Brown | A61B 5/363 607/14 |
| 2010/0179444 A1 | 7/2010 | O'Brien et al. | |
| 2010/0217141 A1* | 8/2010 | Ostrow | G16H 15/00 600/515 |
| 2010/0268103 A1 | 10/2010 | McNamara et al. | |
| 2010/0280841 A1 | 11/2010 | Dong et al. | |
| 2011/0270109 A1 | 11/2011 | Zhang et al. | |
| 2012/0004563 A1 | 1/2012 | Kim et al. | |
| 2012/0209126 A1 | 8/2012 | Amos et al. | |
| 2013/0274524 A1 | 10/2013 | Dakka et al. | |
| 2013/0274624 A1* | 10/2013 | Mahajan | A61B 5/686 600/518 |
| 2014/0257063 A1 | 9/2014 | Ong et al. | |
| 2014/0378856 A1 | 12/2014 | Koike et al. | |
| 2015/0164349 A1 | 6/2015 | Gopalakrishnan et al. | |
| 2015/0216435 A1 | 8/2015 | Bokan et al. | |
| 2015/0265217 A1 | 9/2015 | Penders et al. | |
| 2016/0022164 A1 | 1/2016 | Brockway et al. | |
| 2016/0135706 A1* | 5/2016 | Sullivan | A61B 5/7267 600/509 |
| 2016/0192853 A1 | 7/2016 | Bardy et al. | |
| 2016/0220137 A1 | 8/2016 | Mahajan et al. | |
| 2016/0232280 A1 | 8/2016 | Apte et al. | |
| 2017/0095673 A1 | 4/2017 | Ludwig et al. | |
| 2017/0105683 A1 | 4/2017 | Xue | |
| 2017/0156592 A1 | 6/2017 | Fu | |
| 2017/0196458 A1 | 7/2017 | Ternes et al. | |
| 2017/0265765 A1 | 9/2017 | Baumann et al. | |
| 2017/0290550 A1 | 10/2017 | Perschbacher et al. | |
| 2017/0347894 A1 | 12/2017 | Bhushan et al. | |
| 2017/0354365 A1 | 12/2017 | Zhou | |
| 2018/0008976 A1 | 3/2018 | Okazaki | |
| 2018/0089763 A1 | 3/2018 | Okazaki | |
| 2018/0146874 A1 | 5/2018 | Walker et al. | |
| 2018/0146929 A1 | 5/2018 | Joo et al. | |
| 2018/0206721 A1* | 7/2018 | Zhang | A61B 5/746 |
| 2018/0233227 A1 | 8/2018 | Galloway et al. | |
| 2018/0272147 A1* | 9/2018 | Freeman | G16H 50/30 |
| 2018/0279891 A1 | 10/2018 | Miao et al. | |
| 2018/0310892 A1 | 11/2018 | Perschbacher et al. | |
| 2019/0008461 A1 | 1/2019 | Gupta et al. | |
| 2019/0029552 A1 | 1/2019 | Perschbacher et al. | |
| 2019/0038148 A1 | 2/2019 | Valys et al. | |
| 2019/0038149 A1 | 2/2019 | Gopalakrishnan et al. | |
| 2019/0090774 A1 | 3/2019 | Yang et al. | |
| 2019/0122097 A1* | 4/2019 | Shibahara | G06N 3/0454 |
| 2019/0209022 A1 | 7/2019 | Sobol et al. | |
| 2019/0272920 A1 | 9/2019 | Teplitzky | |
| 2019/0275335 A1 | 9/2019 | Volpe et al. | |
| 2019/0328251 A1* | 10/2019 | Jin | A61B 5/02405 |
| 2019/0343415 A1 | 11/2019 | Saha et al. | |
| 2019/0365342 A1* | 12/2019 | Ghaffarzadegan | A61B 7/04 |
| 2019/0378620 A1 | 12/2019 | Saren | |
| 2020/0100693 A1 | 4/2020 | Velo | |
| 2020/0108260 A1 | 4/2020 | Haddad et al. | |
| 2020/0178825 A1 | 6/2020 | Weijia et al. | |
| 2020/0288997 A1 | 9/2020 | Shute et al. | |
| 2020/0352462 A1 | 11/2020 | Pedalty et al. | |
| 2020/0352466 A1 | 11/2020 | Chakravarthy et al. | |
| 2020/0352521 A1 | 11/2020 | Chakravarthy et al. | |
| 2020/0353271 A1 | 11/2020 | Dani et al. | |
| 2020/0357517 A1 | 11/2020 | Haddad et al. | |
| 2020/0357518 A1 | 11/2020 | Musgrove et al. | |
| 2020/0357519 A1 | 11/2020 | Chakravarthy et al. | |
| 2021/0137384 A1 | 5/2021 | Robinson et al. | |
| 2021/0169736 A1 | 6/2021 | Wijshoff et al. | |
| 2021/0204858 A1 | 7/2021 | Attia et al. | |
| 2021/0338134 A1 | 11/2021 | Chakravarthy et al. | |
| 2021/0338138 A1 | 11/2021 | Pedalty et al. | |
| 2021/0343416 A1 | 11/2021 | Chakravarthy et al. | |
| 2021/0345865 A1 | 11/2021 | Spillinger et al. | |
| 2021/0358631 A1 | 11/2021 | Haddad et al. | |

FOREIGN PATENT DOCUMENTS

| | | |
|---|---|---|
| EP | 2427105 A1 | 3/2012 |
| WO | 2010129447 A1 | 11/2010 |
| WO | 2013/160538 A1 | 10/2013 |
| WO | 2017072250 A1 | 5/2017 |
| WO | 2017091736 A1 | 6/2017 |
| WO | 2018119316 A1 | 6/2018 |
| WO | 2020049267 A1 | 3/2020 |

OTHER PUBLICATIONS

Bresnick, "Machine Learning Algorithm Outperforms Cardiologists Reading EKGs", Health IT Analytics, Jul. 12, 2017, p. 5.

Notice of Allowance from U.S. Appl. No. 17/389,831, dated Apr. 25, 2022, 5 pp.

Office Action from U.S. Appl. No. 16/832,732, dated Mar. 2, 2022, 16 pp.

Response to Final Office Action dated Mar. 2, 2022, from U.S. Appl. No. 16/851,500, filed May 27, 2022, 19 pp.

Response to Office Action dated Mar. 2, 2022, from U.S. Appl. No. 16/832,732, filed May 23, 2022, 10 pp.

"Classify ECG Signals Using Long Short-Term Memory Networks," MATLAB, retrieved from https://www.mathworks.com/help/signal/examples/classify-ecg-signals-using-long-short-term-memory-networks.html, Nov. 2, 2018, 19 pp.

"Visualize Features of a Convolutional Neural Network," MATLAB & Simulink, Mar. 15, 2018, 9 pp.

Fawaz et al., "Deep learning for time series classification: a review," Irirmas, Universite Haute Alsace, Dec. 7, 2018, 53 pp.

Kelwade et al., "Prediction of Cardiac Arrhythmia using Artificial Neural Network," International Journal of Computer Applications (0975-8887), vol. 115—No. 20, Apr. 2015, 6 pp.

Lau et al., "Connecting the Dots: From Big Data to Healthy Heart," Circulation, vol. 134, No. 5, Aug. 2, 2017, 5 pp.

Schwab et al., "Beat by Beat: Classifying Cardiac Arrhythmias with Recurrent Neural Networks," 2017 Computing in Cardiology (CinC), vol. 44, Oct. 24, 2017, 4 pp.

U.S. Appl. No. 16/593,739, filed Oct. 4, 2019 by Haddad et al.
U.S. Appl. No. 62/843,707, filed May 6, 2019 by Dani et al.
U.S. Appl. No. 62/843,738, filed May 6, 2019 by Chakravarthy et al.
U.S. Appl. No. 62/843,702, filed May 6, 2019 by Musgrove et al.
U.S. Appl. No. 62/843,717, filed May 6, 2019 by Chakravarthy et al.
U.S. Appl. No. 62/843,730, filed May 6, 2019 by Pedalty et al.
U.S. Appl. No. 16/832,732, filed Mar. 27, 2020 by Chakravarthy et al.

(56) References Cited

OTHER PUBLICATIONS

Chen, Electrocardiogram Recognition Based on Variational AutoEncoder, Aug. 29, 2018, Machine Learning and Biometrics, IntechOpen, pp. 71-90.
Final Office Action from U.S. Appl. No. 16/851,500, dated Mar. 2, 2022, 41 pp.
International Preliminary Report on Patentability from International Application No. PCT/US2020/027954, dated Nov. 18, 2021, 8 pp.
Notice of Allowance from U.S. Appl. No. 17/389,831, dated Jan. 5, 2022, 5 pp.
Office Action from U.S. Appl. No. 16/851,500, dated Sep. 21, 2021, 76 pp.
Response to Office Action dated Sep. 10, 2021, from U.S. Appl. No. 17/389,831, filed Dec. 10, 2021, 17 pp.
Response to Office Action dated Sep. 21, 2021, from U.S. Appl. No. 16/851,500, filed Dec. 21, 2021, 19 pp.
Swerdlow et al., "Troubleshooting Implanted Cardioverter Defibrillator Sensing Problems I," Circ Arrhythm Electrophysiol., vol. 7, No. 6, Dec. 2014, pp. 1237-1261.
International Search Report and Written Opinion of International Application No. PCT/US2020/027954, dated Jul. 27, 2020, 13 pp.
Andersen et al., "A Deep Learning Approach for Real-Time Detection of Atrial Fibrillation," Expert Systems with Applications, vol. 114, Aug. 14, 2018, pp. 465-473.
Schirrmeisteret al., "Deep Learning with Convolutional Neural Networks for Brain Mapping and Decoding of Movement-Related Information from the Human EEG," Cornell University Library, Mar. 16, 2017, 58 pp.
Madani et al., "Fast and Accurate View Classification of Echocardiograms Using Deep Learning," Nature Partner Journals, vol. 1, No. 6, Mar. 21, 2018, 8 pp.
U.S. Appl. No. 16/850,833, filed Apr. 16, 2020 by Dani et al.
U.S. Appl. No. 16/850,699, filed Apr. 16, 2020 by Chakravarthy et al.
U.S. Appl. No. 16/851,500, filed Apr. 17, 2020 by Musgrove et al.
U.S. Appl. No. 16/851,603, filed Apr. 17, 2020 by Chakravarthy et al.
U.S. Appl. No. 16/850,749, filed Apr. 16, 2020 by Pedalty et al.
Notice of Allowance from U.S. Appl. No. 16/851,500, dated Jun. 14, 2022, 12 pp.
Office Action from U.S. Appl. No. 16/850,833 dated Jun. 23, 2022, 27 pp.
U.S. Appl. No. 17/373,480, filed Jul. 12, 2021, naming inventors Chakravarthy et al.
U.S. Appl. No. 17/377,785, filed Jul. 16, 2021, Pedalty et al.
U.S. Appl. No. 17/389,831, filed Jul. 30, 2021, by Haddad et al.
U.S. Appl. No. 17/377,763, filed Jul. 16, 2021, naming inventors Chakravarthy et al.
Isin et al., "Cardiac Arrhythmia Detection Using Deep Learning," Procedia Computer Science vol. 120, 2017 Applicant points out, in accordance with MPEP 609.04(a), that the year of publication, 2017, is sufficiently earlier than the effective U.S. filing date, so that the particular month of publication is not in issue.) pp. 268-275.
Arrobo et al., "An Innovative Wireless Cardiac Rhythm Management (iCRM) System," Computer Science, 2014 Wireless Telecommunications Symposium, Jun. 2014, 5 pp.
Swerdlow et al., "An Innovative Wireless Cardiac Rhythm Management (iCRM) System," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
Office Action from U.S. Appl. No. 17/389,831, dated Sep. 10, 2021, 22 pp.
Advisory Action from U.S. Appl. No. 16/832,732 dated Nov. 16, 2022, 3 pp.
Final Office Action from U.S. Appl. No. 16/832,732 dated Sep. 1, 2022, 10 pp.
Notice of Allowance from U.S. Appl. No. 16/850,833 dated Oct. 19, 2022, 10 pp.
Response to Final Office Action dated Sep. 1, 2022 from U.S. Appl. No. 16/832,732, filed Nov. 1, 2022, 14 pp.
Response to Office Action dated Jun. 23, 2022 from U.S. Appl. No. 16/850,833, filed Sep. 22, 2022, 14 pp.
Advisory Action from U.S. Appl. No. 16/832,732 dated Dec. 13, 2022, 3 pp.
Anonymous, "Receiver Operating Characteristic—Wikipedia," Mar. 20, 2019, Retrieved from the Internet: URL https://en.wikipedia.org/w/index.php?title=Receiver_operating_characteristic&oldis=888671034#History, 12 pp.
Habibzadeh et al., "On Determining the Most Appropriate Test Cut-Off Value: the Case of Tests with Continuous Results," Biochemia Medica, Oct. 15, 2016, pp. 297-307.
Office Action from U.S. Appl. No. 16/832,732 dated Jan. 13, 2023, 9 pp.
Response to Final Office Action dated Mar. 2, 2022, from U.S. Appl. No. 16/851,500, filed May 2, 2022, 19 pp.
Response to Final Office Action dated Sep. 1, 2022 from U.S. Appl. No. 16/832,732, filed Nov. 30, 2022, 16 pp.
Witten et al., "Data mining: Practical Machine Learning Tools and Techniques," Third Edition, Morgan Kaufmann, Feb. 3, 2011, 665 pp.
Response to Office Action dated Jan. 13, 2023 from U.S. Appl. No. 16/832,732, filed Apr. 12, 2023, 19 pp.

* cited by examiner

MACHINE LEARNING BASED DEPOLARIZATION IDENTIFICATION AND ARRHYTHMIA LOCALIZATION VISUALIZATION

This application claims the benefit of U.S. Provisional Application Ser. No. 62/843,786, filed May 6, 2019, the entire content of which is incorporated herein by reference.

FIELD

This disclosure generally relates to medical devices and, more particularly, analysis of signals sensed by medical devices.

BACKGROUND

Medical devices may be used to monitor physiological signals of a patient. For example, some medical devices are configured to sense cardiac electrogram (EGM) signals, e.g., electrocardiogram (ECG) signals, indicative of the electrical activity of the heart via electrodes. Some medical devices are configured to detect occurrences of cardiac arrhythmia, often referred to as episodes, based on the cardiac EGM and, in some cases, data from additional sensors. Example arrhythmia types include asystole, bradycardia, ventricular tachycardia, supraventricular tachycardia, wide complex tachycardia, atrial fibrillation, atrial flutter, ventricular fibrillation, atrioventricular block, premature ventricular contractions, and premature atrial contractions. The medical devices may store the cardiac EGM and other data collected during a time period including an episode as episode data. The medical device may also store episode data for a time period in response to user input, e.g., from the patient.

A computing system may obtain episode data from medical devices to allow a clinician or other user to review the episode. A clinician may diagnose a medical condition of the patient based on identified occurrences of cardiac arrhythmias within the episode. In some examples, a clinician or other reviewer may review episode data to annotate the episodes, including determining whether arrhythmias detected by the medical device actually occurred, to prioritize the episodes and generate reports for further review by the clinician that prescribed the medical device for a patient or is otherwise responsible for the care of the particular patient.

SUMMARY

In general, this disclosure describes techniques for classifying, annotating, reporting episode data, including cardiac EGM data, using one or more machine learning models. In some examples, processing circuitry applies one or more arrhythmia classification machine learning models to the episode data. The one or more machine learning models output a respective likelihood value representing the likelihood that a respective arrhythmia type classification occurred at any point during the episode. The processing circuitry also derives class activation data for each arrhythmia type classification indicating varying likelihoods of the classification over the period of time, and may display a graph of the varying likelihoods over the period of time. The displayed graph of likelihoods over time may aid a user in understanding the reasoning for any arrhythmia detections during the episode, particularly when displayed in conjunction with the underlying cardiac EGM.

In some examples, the processing circuitry applies one or more depolarization detection machine learning models to the episode data. The one or more depolarization detection machine learning models are configured to output a set of depolarization likelihood values representing the likelihood of a depolarization at different times during the episode. The processing circuitry may use both depolarization and arrhythmia type classification likelihood values to enhance its ability to detect depolarizations during the episode.

In one example, this disclosure describes a computer-implemented method comprising receiving, by processing circuitry of a medical device system, episode data for an episode stored by a medical device of a patient, wherein the episode is associated with a period of time, and the episode data comprises a cardiac electrogram sensed by the medical device during the period of time. The method further comprises applying, by the processing circuitry, one or more machine learning models to the episode data, the one or more machine learning models configured to output a respective likelihood value for each of a plurality of arrhythmia type classifications, each of the likelihood values representing a likelihood that the respective arrhythmia type classification occurred at any point during the period of time. The method further comprises, based on the application of the one or more machine learning models to the episode data, deriving, by the processing circuitry and for each of the arrhythmia type classifications, class activation data indicating varying likelihoods of the classification over the period of time. The method further comprises displaying, by the processing circuitry and to a user, a graph of the varying likelihoods of the arrhythmia type classifications over the period of time.

In another example, a computer-implemented method comprises receiving, by processing circuitry of a medical device system, episode data for an episode stored by a medical device of a patient, wherein the episode is associated with a period of time, and the episode data comprises a cardiac electrogram sensed by the medical device during the period of time. The method further comprises applying, by the processing circuitry, one or more arrhythmia classification machine learning models to the episode data, the one or more arrhythmia classification machine learning models configured to output, for each of a plurality of arrhythmia type classifications, a respective set of arrhythmia type likelihood values, each of the arrhythmia type likelihood values of the set representing a likelihood that the respective arrhythmia type classification occurred at a respective time during the period of time. The method further comprises applying, by the processing circuitry, one or more depolarization detection machine learning models to the episode data, the one or more depolarization detection machine learning models configured to output a set of depolarization likelihood values, each of the depolarization likelihood values of the set representing the likelihood that a depolarization occurred at a respective time during the period of time. The method further comprises identifying, by the processing circuitry, one or more depolarizations during the episode based on the arrhythmia type likelihood values and depolarization likelihood values.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

A variety of types of implantable and external medical devices detect arrhythmia episodes based on sensed cardiac EGMs and, in some cases, other physiological parameters. External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data, e.g., episode data for detected arrhythmia episodes, to a remote patient monitoring system, such as the Medtronic Carelink™ Network.

Implantable medical devices (IMDs) also sense and monitor cardiac EGMs, and detect arrhythmia episodes. Example IMDs that monitor cardiac EGMs include pacemakers and implantable cardioverter-defibrillators, which may be coupled to intravascular or extravascular leads, as well as pacemakers with housings configured for implantation within the heart, which may be leadless. Some IMDs that do not provide therapy, e.g., implantable patient monitors, sense cardiac EGMs. One example of such an IMD is the Reveal LINQ™ Insertable Cardiac Monitor (ICM), available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

By uploading episode data from medical devices, and distributing the episode data to various users, such network services may support centralized or clinic-based arrhythmia episode review, annotation, and reporting. The episode data may include an indication of the one or more arrhythmias that the medical device detected during the episode. The episode data may also include data collected by the medical device during a time period including time before and after the instant the medical device determined the one or more arrhythmias to have occurred. The episode data may include the digitized cardiac EGM during that time period, heart rates or other parameters derived from the EGM during that time period, and any other physiological parameter data collected by the medical device during the time period.

Figure 1:
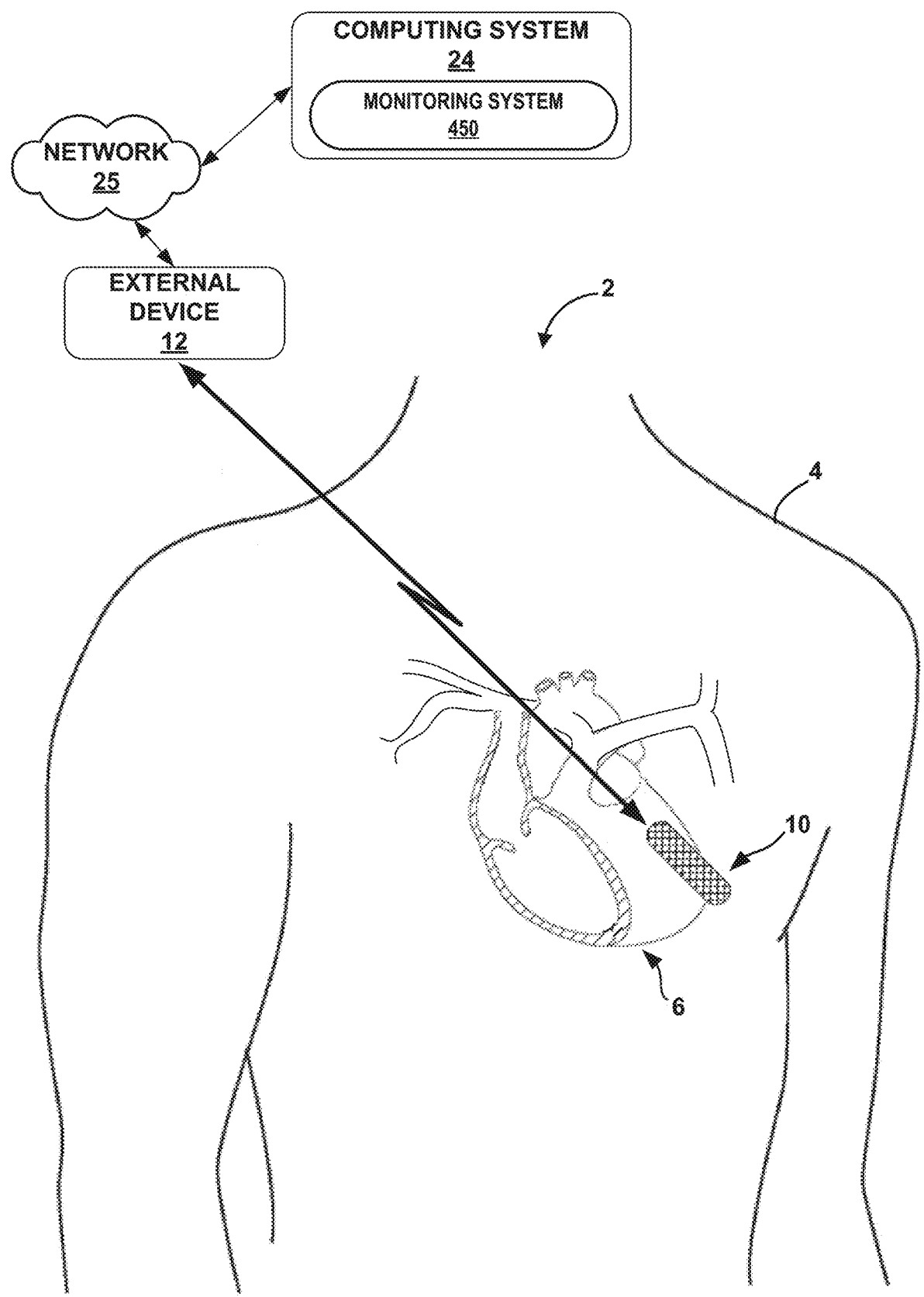
FIG. 1 is a conceptual drawing illustrating an example of a medical device system configured to utilize machine learning models to detect cardiac depolarizations and arrhythmias in accordance with the techniques of the disclosure.

FIG. 1 is a conceptual drawing illustrating an example of a medical device system 2 configured to utilize machine learning models to detect cardiac depolarizations and arrhythmias in accordance with the techniques of the disclosure. The example techniques may be used with an IMD 10, which may be in wireless communication with an external device 12. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM. Although described primarily in the context of examples in which the medical device that collects episode data takes the form of an ICM, the techniques of this disclosure may be implemented in systems including any one or more implantable or external medical devices, including monitors, pacemakers, or defibrillators.

External device 12 is a computing device configured for wireless communication with IMD 10. External device 12 may be configured to communicate with computing system 24 via network 25. In some examples, external device 12 may provide a user interface and allow a user to interact with IMD 10. Computing system 24 may comprise computing devices configured to allow a user to interact with IMD 10, or data collected from IMD, via network 25

External device 12 may be used to retrieve data from IMD 10 and may transmit the data to computing system 24 via network 25. The retrieved data may include values of physiological parameters measured by IMD 10, indications of episodes of arrhythmia or other maladies detected by IMD 10, episode data collected for episodes, and other physiological signals recorded by IMD 10. The episode data may include EGM segments recorded by IMD 10, e.g., due to IMD 10 determining that an episode of arrhythmia or another malady occurred during the segment, or in response to a request to record the segment from patient 4 or another user.

In some examples, computing system 24 includes one or more handheld computing devices, computer workstations, servers or other networked computing devices. In some examples, computing system 24 may include one or more devices, including processing circuitry and storage devices, that implement a monitoring system 450. Computing system 24, network 25, and monitoring system 450 may be implemented by the Medtronic Carelink™ Network or other patient monitoring system, in some examples.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing system 24 and IMD 10, access to the Internet, and may provide a communication framework that allows the computing devices to communicate with one another. In some examples, network 25 may be a private network that provides a communication framework that allows computing system 24, IMD 10, and/or external device 12 to communicate with one another but isolates one or more of computing system 24, IMD 10, or external device 12 from devices external to network 25 for security purposes. In some examples, the communications between computing system 24, IMD 10, and external device 12 are encrypted.

Monitoring system 450, e.g., implemented by processing circuitry of computing system 24, may implement the techniques of this disclosure including applying machine learning models to episode data to detect cardiac depolarizations and arrhythmias. Monitoring system 450 may receive episode data for episodes from medical devices, including IMD 10, which may store the episode data in response to their detection of an arrhythmia and/or user input. Based on the application of one or more arrhythmia classification machine learning models, monitoring system 450 may determine the likelihood that one or more arrhythmias of one or more types occurred during the episode including, in some examples, the arrhythmia identified by the medical device that stored the episode data.

Monitoring system 450 may also derive and plot activation data indicating the likelihoods of various arrhythmia type classifications over the time period of the episode, and apply one or more depolarization detection machine learning models to the episode data to identify the occurrence of depolarizations, e.g., R-waves or QRS complexes, during the episode. Monitoring system 450 may display, e.g., in conjunction, one or more of the arrhythmia type classifications, arrhythmia type classification likelihood plots, markers indicating the times of identified depolarizations, and the cardiac EGM for the episode, which may facilitate a user's review and comprehension of the episode data the classification(s) by monitoring system 450. Although the techniques are described herein as being performed by monitoring system 450, and thus by processing circuitry of computing system 24, the techniques may be performed by processing circuitry of any one or more devices or systems of a medical device system, such as computing system 24, external device 12, or IMD 10. The machine learning models may include, as examples, neural networks, deep learning models, convolutional neural networks, or other types of predictive analytics systems.

Figure 2:
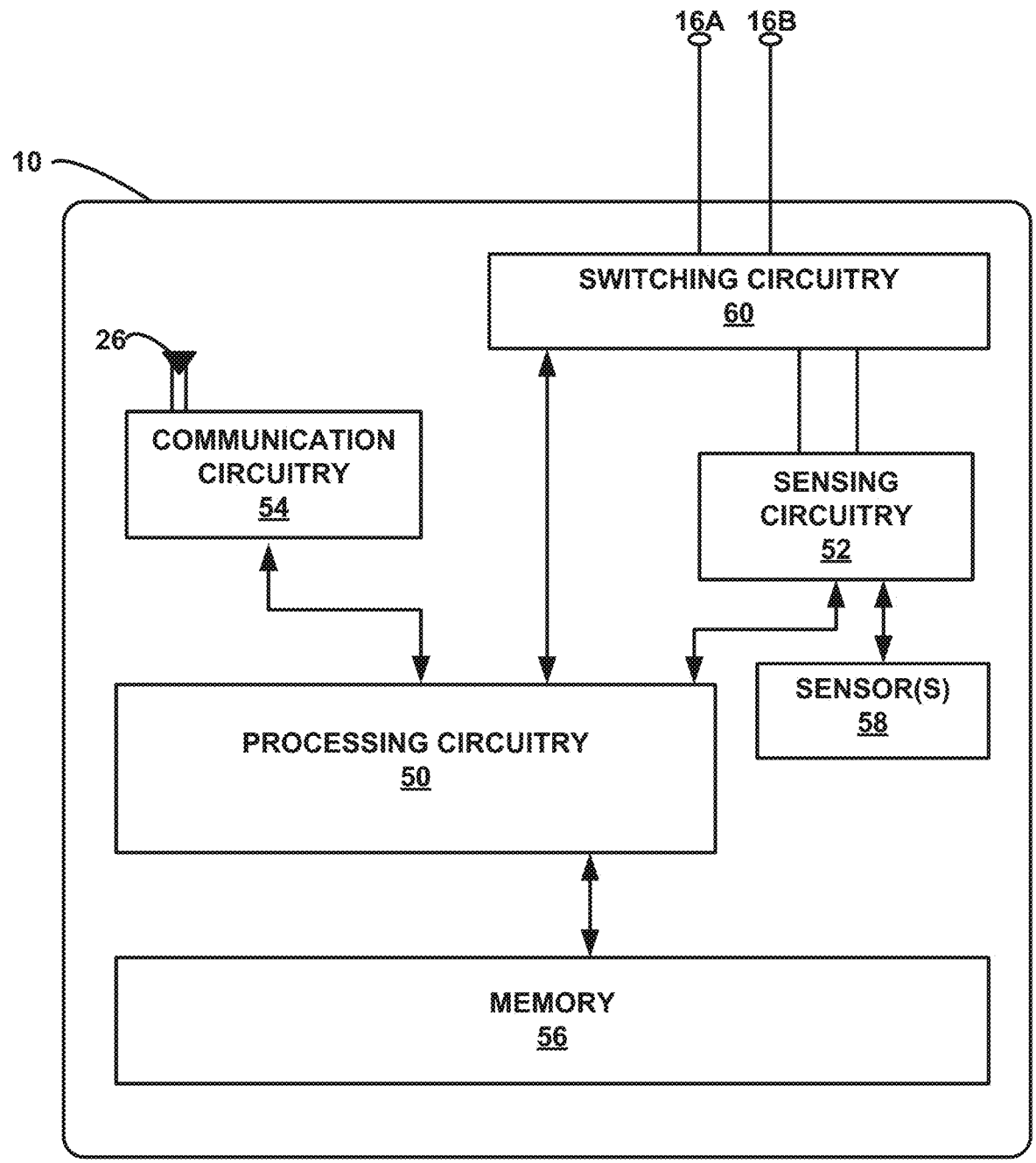
FIG. 2 is a block diagram illustrating an example configuration of the implantable medical device (IMD) of FIG. 1.

FIG. 2 is a block diagram illustrating an example configuration of IMD 10 of FIG. 1. As shown in FIG. 2, IMD 10 includes processing circuitry 50 sensing circuitry 52, communication circuitry 54, memory 56, sensors 58, switching circuitry 60, and electrodes 16A, 16B (hereinafter "electrodes 16"), one or more of which may be disposed on a housing of IMD 10. In some examples, memory 56 includes computer-readable instructions that, when executed by processing circuitry 50, cause IMD 10 and processing circuitry 50 to perform various functions attributed herein to IMD 10 and processing circuitry 50. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce cardiac EGM data for patient 4. In some examples, processing circuitry 50 may identify features of the sensed cardiac EGM to detect an episode of cardiac arrhythmia of patient 4. Processing circuitry 50 may store the digitized cardiac EGM and features of the EGM used to detect the arrhythmia episode in memory 56 as episode data for the detected arrhythmia episode. In some examples, processing circuitry 50 stores one or more segments of the cardiac EGM data, features derived from the cardiac EGM data, and other episode data in response to instructions from external device 12 (e.g., when patient 4 experiences one or more symptoms of arrhythmia and inputs a command to external device 12 instructing IMD 10 to upload the data for analysis by a monitoring center or clinician).

In some examples, processing circuitry 50 transmits, via communication circuitry 54, the episode data for patient 4 to an external device, such as external device 12 of FIG. 1. For example, IMD 10 sends digitized cardiac EGM and other episode data to network 25 for processing by monitoring system 450 of FIG. 1.

Sensing circuitry 52 and/or processing circuitry 50 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 52 may include a rectifier, filter, amplifier, comparator, and/or analog-to-digital converter, in some examples. In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining features of the cardiac EGM including inter-depolarization intervals, heart rate, and detecting arrhythmias, such as tachyarrhythmias and asystole. Sensing circuitry 52 may also provide one or more digitized cardiac EGM signals to processing circuitry 50 for analysis, e.g., for use in cardiac rhythm discrimination and/or to identify and delineate features of the cardiac EGM, such as QRS amplitudes and/or width, or other morphological features.

In some examples, IMD 10 includes one or more sensors 58, such as one or more accelerometers, microphones, optical sensors, and/or pressure sensors. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter. Processing circuitry 50 may determine values of physiological parameters of patient 4 based on signals from sensors 58, which may be used to identify arrhythmia episodes and stored as episode data in memory 56.

Communication circuitry 54 may include any suitable hardware, firmware, software or any combination thereof for communicating with another device, such as external device 12. Under the control of processing circuitry 50, communication circuitry 54 may receive downlink telemetry from, as well as send uplink telemetry to, external device 12 or another device with the aid of an internal or external antenna, e.g., antenna 26. In some examples, processing circuitry 50 may communicate with a networked computing device via an external device (e.g., external device 12) and a computer network, such as the Medtronic CareLink® Network developed by Medtronic, plc, of Dublin, Ireland.

Although described herein in the context of example IMD 10, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a medical device external to patient 4, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses, a "smart" patch, or a "smart" watch.

Figure 3:
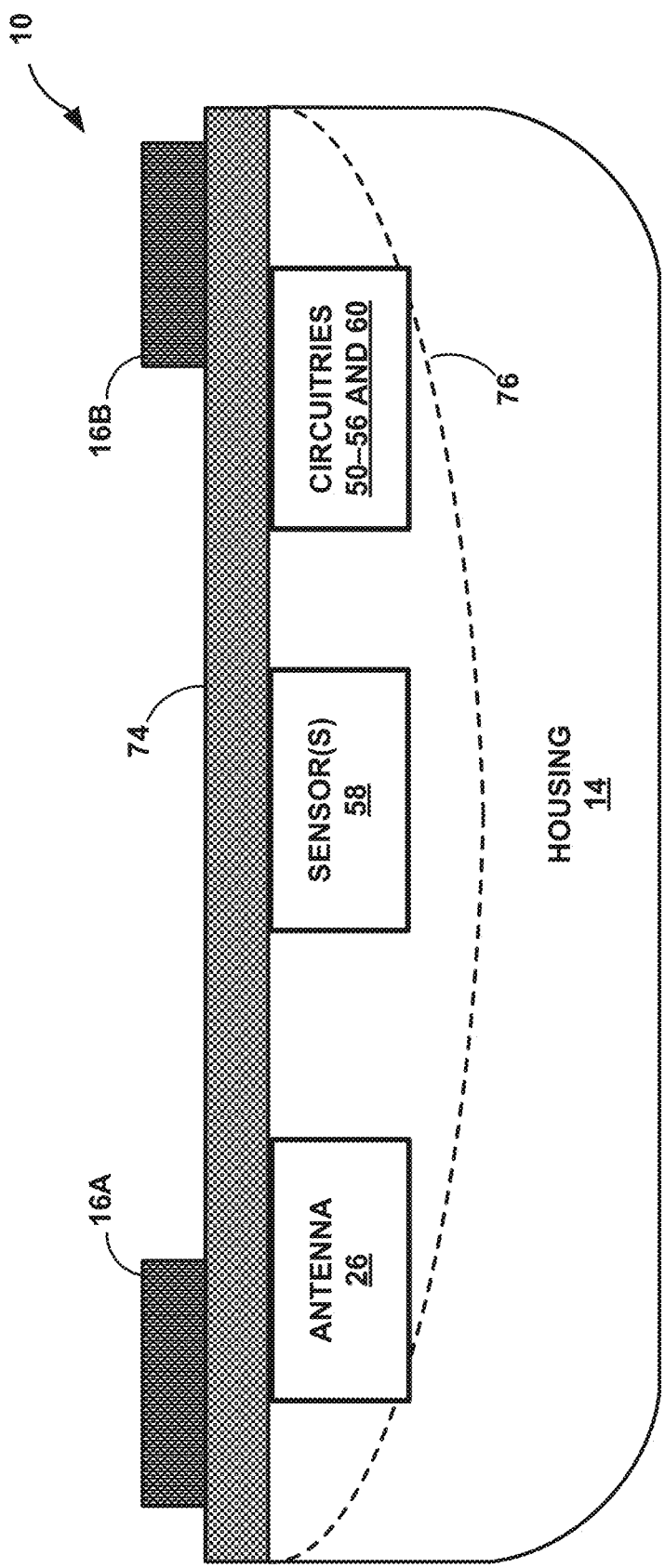
FIG. 3 is a conceptual side-view diagram illustrating an example configuration of the IMD of FIGS. 1 and 2.

FIG. 3 is a conceptual side-view diagram illustrating an example configuration of IMD 10. In the example shown in FIG. 3, IMD 10 may include a leadless, subcutaneously-implantable monitoring device having a housing 14 and an insulative cover 74. Electrode 16A and electrode 16B may be formed or placed on an outer surface of cover 74. Circuitries 50-56 and 60, described above with respect to FIG. 2, may be formed or placed on an inner surface of cover 74, or within housing 14. In the illustrated example, antenna 26 is formed or placed on the inner surface of cover 74, but may be formed or placed on the outer surface in some examples. Sensors 58 may also be formed or placed on the inner or outer surface of cover 74 in some examples. In some examples, insulative cover 74 may be positioned over an open housing 14 such that housing 14 and cover 74 enclose antenna 26, sensors 58, and circuitries 50-56 and 60, and protect the antenna and circuitries from fluids such as body fluids.

One or more of antenna 26, sensors 58, or circuitries 50-56 may be formed on insulative cover 74, such as by using flip-chip technology. Insulative cover 74 may be flipped onto a housing 14. When flipped and placed onto housing 14, the components of IMD 10 formed on the inner side of insulative cover 74 may be positioned in a gap 76 defined by housing 14. Electrodes 16 may be electrically connected to switching circuitry 60 through one or more vias (not shown) formed through insulative cover 74. Insulative cover 74 may be formed of sapphire (i.e., corundum), glass, parylene, and/or any other suitable insulating material. Housing 14 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
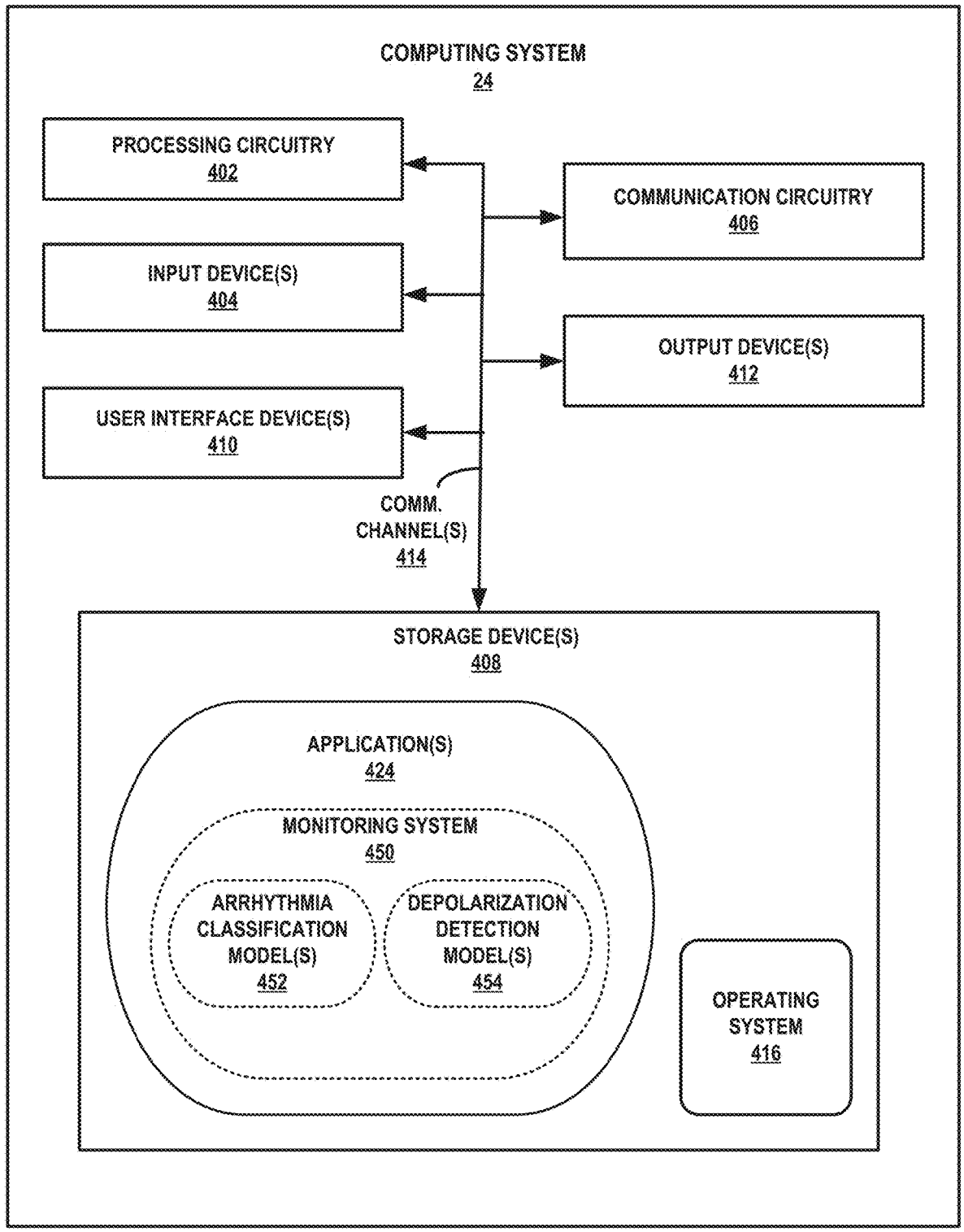
FIG. 4 is a functional block diagram illustrating an example configuration of the computing system of FIG. 1.

FIG. 4 is a block diagram illustrating an example configuration of computing system 24. In the illustrated example, computing system 24 includes processing circuitry 402 for executing applications 424 that include monitoring system 450 or any other applications described herein. Computing system 24 may be any component or system that includes processing circuitry or other suitable computing environment for executing software instructions and, for example, need not necessarily include one or more elements shown in FIG. 4 (e.g., input devices 404, communication circuitry 406, user interface devices 410, or output devices 412; and in some examples components such as storage device(s) 408 may not be co-located or in the same chassis as other components). In some examples, computing system 24 may be a cloud computing system distributed across a plurality of devices.

In the example of FIG. 4, computing system 24 includes processing circuitry 402, one or more input devices 404, communication circuitry 406, one or more storage devices 408, user interface (UI) device(s) 410, and one or more output devices 412. Computing system 24, in some examples, further includes one or more application(s) 424 such as monitoring system 450, and operating system 416 that are executable by computing system 24. Each of components 402, 404, 406, 408, 410, and 412 may be coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing system 24. For example, processing circuitry 402 may be capable of processing instructions stored in storage device 408. Examples of processing circuitry 402 may include any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing device 400 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing system 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable memories (EEPROM).

Computing system 24, in some examples, also includes communication circuitry 406 to communicate with other devices and systems, such as IMD 10 and external device 12 of FIG. 1. Communication circuitry 406 may include a network interface card, such as an Ethernet card, an optical transceiver, a radio frequency transceiver, or any other type of device that can send and receive information. Other examples of such network interfaces may include 3G and WiFi radios.

Computing system 24, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing system 24. Output devices 412, in some examples, are configured to provide output to a user using tactile, audio, or video stimuli. Output devices 412, in one example, include a presence-sensitive display, a sound card, a video graphics adapter card, or any other type of device for converting a signal into an appropriate form understandable to humans or machines. Additional examples of output devices 412 include a speaker, a cathode ray tube (CRT) monitor, a liquid crystal display (LCD), or any other type of device that can generate intelligible output to a user.

Computing system 24 may include operating system 416. Operating system 416, in some examples, controls the operation of components of computing system 24. For example, operating system 416, in one example, facilitates the communication of one or more applications 424 and monitoring system 450 with processing circuitry 402, communication circuitry 406, storage device 408, input device 404, user interface devices 410, and output device 412.

Applications 424 may also include program instructions and/or data that are executable by computing device 400. Example application(s) 424 executable by computing device 400 may include monitoring system 450. Other additional applications not shown may alternatively or additionally be included to provide other functionality described herein and are not depicted for the sake of simplicity.

In accordance with the techniques of the disclosure, computing system 24 receives episode data for episodes stored by medical devices, such as IMD 10, via communication circuitry 406. Storage device 408 may store the episode data for the episodes in storage device 408. The episode data may have been collected by the medical devices in response to the medical devices detecting arrhythmias and/or user input directing the storage of episode data.

Monitoring system 450, as implemented by processing circuitry 402, may review and annotate the episodes, and generate of reports or other presentations of the episodes subsequent to the annotation for review by a clinician or other reviewer. Monitoring system 450 may utilize input devices 404, output devices 412, and/or communication circuitry 406 to display episode data, arrhythmia type classifications, plots, identified depolarizations, and any other information described herein to users, and to receive any annotations or other input regarding the episode data from the users.

To review and annotate episodes, monitoring system 450 may apply the episode data as inputs to a selected one or more machine learning models. In the example illustrated by FIG. 4, monitoring system 450 may apply episode data to one or more arrhythmia classification machine learning models 452 and/or one or more depolarization detection models 454. Machine learning models 452 and 454 may include, as examples, neural networks, such as deep neural networks, which may include convolutional neural networks, multi-layer perceptrons, and/or echo state networks, as examples.

Arrhythmia classification machine learning models 452 may be configured to output, for each of a plurality of arrhythmia type classifications, values indicative of the likelihood that an arrhythmia of the type occurred at any point during the episode. Monitoring system 450 may apply configurable thresholds (e.g., 50%, 75%, 90%, 95%, 99%) to the likelihood values to annotate the episode as including one or more arrhythmia types, e.g., based on the likelihood for that classification meeting or exceeding the threshold.

In some examples, arrhythmia classification machine learning models 452 are trained with training data that comprises cardiac EGM or other episode data for a plurality of patients labeled with descriptive metadata. For example, during a training phase, monitoring system 450 processes a plurality of cardiac EGM waveforms. Typically, the plurality of cardiac EGM waveforms are from a plurality of different patients, but may be from a single patient. Each cardiac EGM waveform is labeled with one or more episodes of arrhythmia of one or more types.

For example, a training cardiac EGM waveform may include a plurality of segments, each segment labeled with a descriptor that specifies an absence of arrhythmia or a presence of an arrhythmia of a particular classification (e.g., bradycardia, pause, tachycardia, atrial fibrillation, atrial flutter, atrioventricular block, or ventricular fibrillation). In some examples, a clinician labels the presence of arrhythmia in each cardiac EGM waveform by hand. In some examples, the presence of arrhythmia in each cardiac EGM waveform is labeled according to classification by a cardiac EGM feature delineation algorithm, e.g., similar to the techniques used by IMD 10 to identify arrhythmias based on rates, intervals, and morphological features derived from the cardiac EGM.

Monitoring system 450 may operate to convert the training data into vectors and multi-dimensional arrays upon which monitoring system 450 may apply mathematical operations, such as linear algebraic, nonlinear, or alternative computation operations. Monitoring system 450 uses the training data to teach the one or more arrhythmia classification machine learning models 452 to weigh different features depicted in the cardiac EGM data. In some examples, monitoring system 450 uses the cardiac EGM data to teach the machine learning model to apply different coefficients that represent one or more features in a cardiac EGM as having more or less importance with respect to an occurrence of a cardiac arrhythmia of a particular classification. By processing numerous such waveforms labeled with episodes of arrhythmia, monitoring system 450 may build and train one or more arrhythmia classification machine learning models 452 to receive cardiac EGM data from a patient, such as patient 4 of FIG. 1, that monitoring system 450 has not previously analyzed, and process such cardiac EGM data to detect the presence or absence of arrhythmia types of different classifications in the patient with a high degree of accuracy. Typically, the greater the amount of cardiac EGM data on which the one or more arrhythmia classification machine learning models 452 is trained, the higher the accuracy of the machine learning models in detecting or classifying cardiac arrhythmia in new cardiac EGM data.

After monitoring system 450 has trained one or more arrhythmia classification machine learning models 452, monitoring system 450 may receive episode data, such as cardiac electrogram EGM data, for a particular patient, such as patient 4. Monitoring system 450 applies the one or more trained arrhythmia classification machine learning models 452 to the episode data to determine whether one or more arrhythmia types occurred at any point during the episode.

In some examples, monitoring system 450 may process one or more features of the cardiac EGM data instead of, or in addition to, the raw cardiac EGM data itself. The one or more features may be obtained via feature delineation performed by IMD 10 and/or monitoring system 450. The features may include, e.g., one or more of heart rates, inter-depolarization intervals, other intervals between features of the cardiac EGM, one or more amplitudes, widths or morphological features of the QRS wave or other features of the cardiac EGM, variability of any of these features, T-wave alternans, or other types of cardiac features not expressly described herein. In such example implementations, monitoring system 450 may train the one or more arrhythmia classification machine learning models 452 via a plurality of training cardiac features labeled with episodes of arrhythmia, instead of or in addition to the plurality of cardiac EGM waveforms labeled with episodes of arrhythmia as described above.

In further examples, monitoring system 450 may generate, from the cardiac EGM data, an intermediate representation of the cardiac EGM data. For example, monitoring system 450 may apply one or more of signal processing, downsampling, normalization, signal decomposition, wavelet decomposition, filtering, noise reduction, or neural-network based feature representation operations to the cardiac electrogram data to generate the intermediate representation of the cardiac electrogram data. Monitoring system 450 may process such an intermediate representation of the cardiac EGM data to detect and classify arrhythmias of various types in patient 4. Furthermore, monitoring system 450 may train the one or more arrhythmia classification machine learning models 452 via a plurality of training intermediate representations labeled with episodes of arrhythmia, instead of the plurality of raw cardiac EGM waveforms labeled with episodes of arrhythmia as described above. The use of such intermediate representations of the cardiac EGM data may allow for the training and development of lighter-weight, less computationally complex arrhythmia classification machine learning models 452 by monitoring system 450. Further, the use of such intermediate representations of the cardiac electrogram data may require less iterations and fewer training data to build an accurate machine learning model, as opposed to the use of raw cardiac EGM data to train the machine learning model.

In some examples, based on the application of episode data to the one or more arrhythmia classification machine learning models 452, monitoring system 450 may derive, for each of the arrhythmia type classifications, class activation data indicating varying likelihoods of the classification over the period of time of the episode's waveform. For a given arrhythmia type, the amplitude of such likelihood values at different times corresponds to the probability that an arrhythmia is occurring at that time, with higher values corresponding to higher probability.

Class activation mapping may make it possible to identify regions of an input time series, e.g., of cardiac EGM data, that constitute the reason for the time series being given a particular classification by the one or more arrhythmia classification machine learning models 452. A class activation map for a given classification may be a univariate time series where each element (e.g., at each timestamp at the sampling frequency of the input time series) may be a weighted sum or other value derived from the outputs of an intermediate layer of a neural network or other machine learning model. The intermediate layer may be a global average pooling layer and/or last layer prior to the output layer neurons for each classification.

Monitoring system 450 may display, e.g., via output device(s) 412 and/or communication with another device via communication circuitry 406, a graph of the activation data over the time period of the episode. In some examples, monitoring system 450 may display the class activation data in conjunction with, e.g., on the same screen and at the same time, as the input cardiac EGM. While the one or more arrhythmia classification machine learning models 452 may be configured to provide an output that indicates a likelihood of different arrhythmia type classifications occurring during the episode as a whole, the class activation data may allow monitoring system 450 and/or a user to identify a time during an episode and point during the cardiac EGM at which one or more arrhythmias of one or more types likely occurred.

Post-processing of episode data stored by IMD 10 may include identifying the occurrences of depolarizations, e.g., R-waves and/or QRS complexes, within the cardiac EGM data. The identification of depolarizations during post-processing may be different than that by IMD 10 during detection of the episode and storage of the episode data, providing evidence of a possible misclassification of the episode by IMD 10. Annotation of the cardiac EGM data with markers of the occurrence of identified depolarizations may also facilitate review of the episode data by a user and/or monitoring system 450. Feature delineation techniques to detect depolarizations may include filtering the cardiac EGM data, feature extraction (e.g., using a rectified power signal), peak detection, and refractory analysis or other further processing. Such feature delineation may require feature engineering and detection rule development.

According to the example techniques of this disclosure, monitoring system 450 may apply one or more depolarization detection machine learning models 454 to episode data, e.g., cardiac EGM data. Depolarization detection machine learning models 454 may be configured to output a set of depolarization likelihood values, each of the depolarization likelihood values of the set representing the likelihood that a depolarization occurred at a respective time during the period of time. The set of depolarization likelihoods may be expressed as a probability over time, e.g., $p(QRS_{(t)})$ in the case of detection of QRS complexes.

Monitoring system 450 may train the one or more depolarization detection machine learning models 454 using training sets of cardiac EGM data in a similar manner as described above with respect to the training of arrhythmia classification machine learning models 452. The training sets of cardiac EGM data are annotated, e.g., by a user and/or a feature delineation algorithm, to indicate which portions of the cardiac EGM data are depolarizations. When presented with new cardiac EGM data, e.g., from episode data stored by IMD 10 of patient 4, monitoring system 450 may identify one or more depolarizations in the cardiac EGM based on the depolarization likelihood values output by the one or more depolarization detection machine learning models 454. For example, monitoring system 450 may compare the depolarization likelihood values to a configurable and/or adaptive threshold and identify a depolarization when a depolarization likelihood value meets or exceeds the threshold. In some examples, monitoring system 450 may further post-process the depolarization occurrence times identified based on a likelihood threshold. For example, monitoring system 450 may align the identified times with R-wave peaks identified in the cardiac EGM waveform. As another example, monitoring system 450 may apply refractory processing to the identified depolarization times, e.g., to eliminate times that are no greater than a threshold time interval from another candidate time.

In some cases, it may be difficult for monitoring system 450 and the one or more one or more depolarization detection machine learning models 454 to detect particular depolarizations in the cardiac EGM data with high likelihood, e.g., due to smaller sets of training data having depolarization annotations and/or the occurrence of arrhythmias such as tachycardia, pause, and atrial fibrillation, which may change the morphology and rate of depolarizations. To increase the ability of monitoring system 450 to identify depolarizations, monitoring system 450 may identify depolarizations based on both the depolarization likelihood values and arrhythmia type likelihood values over time, e.g., activation data. For example, arrhythmia type likelihood values indicate a relatively high probability of atrial tachycardia at a time in the cardiac EGM data, monitoring system 450 may take one or more actions that result in an effective increase in the depolarization likelihood values, or a decrease in the depolarization detection threshold value to which the depolarization likelihood values are compared, at the time. Such actions may result in an effective conditioning of the likelihood of depolarization on the likelihood of arrhythmia, or certain arrhythmia types. For example, if an arrhythmia classification machine learning model 452 provides a probability $p1(X_{(t)})$ of an arrhythmia type classification X at intervals, e.g., one second, during an episode, and a depolarization detection machine learning model 454 provides a probability $p2(QRS_{(t)})$, the probability of QRS when arrhythmia likelihood is considered may be expressed as $p3(QRS_{(t)}|p1\&p2)$.

Figure 5:
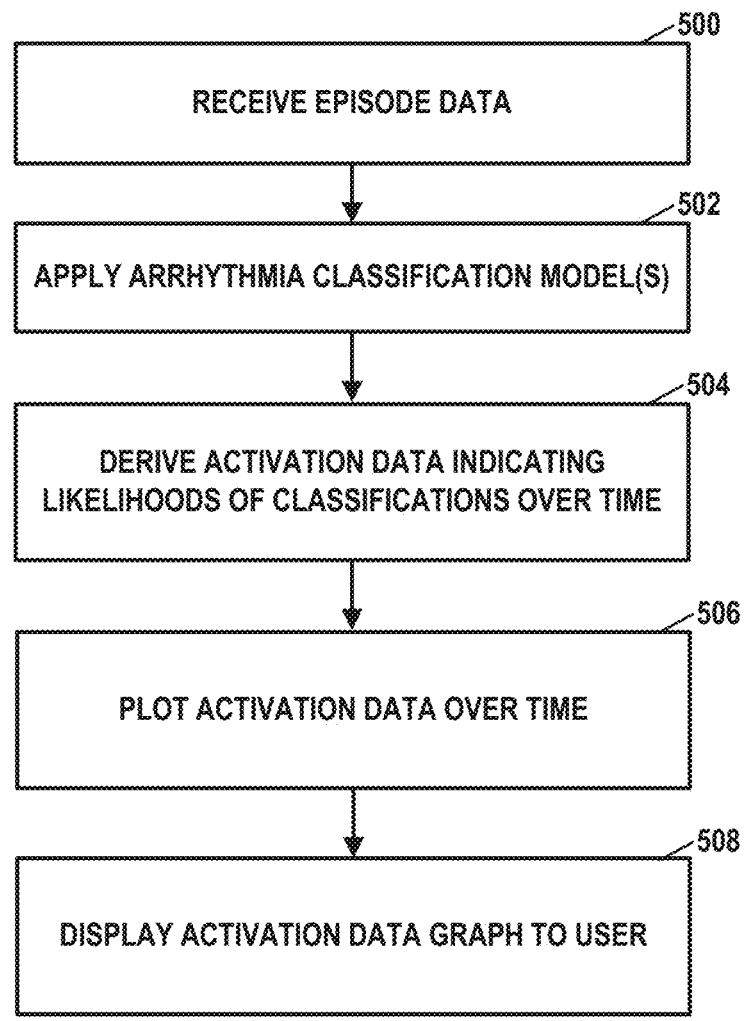
FIG. 5 is a flow diagram illustrating an example operation for providing a visualization of the likelihood of each of a plurality of arrhythmia classifications over time during an episode.

FIG. 5 is a flow diagram illustrating an example operation for providing a visualization of the likelihood of each of a plurality of arrhythmia classifications over time during an episode. For clarity of description, the operations and techniques illustrated by FIGS. 5-9 are described as being performed by monitoring system 450, and thus by processing circuitry 402 of computing system 24. Nevertheless, those operations and techniques, and any others described herein, may be performed by processing circuitry of any one or more devices of medical device system 2, such as IMD 10, external device 12, and computing device 24.

According to the example illustrated by FIG. 5, monitoring system 450 receives episode data recorded by IMD 10 for an episode (500). The episode is associated with a period of time, and the episode data comprises a cardiac EGM sensed by IMD 10 during the period of time. The episode data may include other signals sensed by IMD 10 during the period of time, or data derived from the cardiac EGM or other signal.

Monitoring system 450 applies one or more arrhythmia classification machine learning models 452 to the episode data, e.g., to the cardiac EGM data (502). The one or more arrhythmia classification machine learning models 452 output a respective likelihood value for each of a plurality of arrhythmia type classifications, each of the likelihood values representing the likelihood that the respective arrhythmia type classification occurred at any point during the period of time. Based on the application of the one or more arrhythmia classification machine learning models 452 to the episode data, monitoring system 450 also derives, for each arrhythmia type classification, class activation data indicating varying likelihoods of the classification over the period of time (506). As described herein, monitoring system 450 may derive the activation data from the output of an intermediate layer of machine learning model 452, such as a final layer before the classification layer and/or a global average pooling layer.

Monitoring system 450 plots the activation data for the various arrhythmia type classifications over time (506), and displays a graph of the activation data plots to a user (508). In some examples, monitoring system 450 displays the plot in conjunction with the cardiac EGM for the episode, which may allow a user to correlate times of relatively high likelihood for a particular arrhythmia type with portions of the cardiac EGM causing the relatively high likelihood. In some examples, monitoring system 450 may indicate, e.g., annotate or highlight, times of higher likelihood for at least one of the arrhythmia type classifications relative to other times of the plot for the at least one arrhythmia type classification. In some examples, when monitoring system 450 indicates based on the output of the one or more arrhythmia detection machine learning models 452 that an arrhythmia of a particular type occurred at some unspecified point during an episode, monitoring system 450 may further indicate relatively higher likelihood times for that arrhythmia type classification on the plot of activation data so that a user may understand the reasoning for the classification by the one or more arrhythmia detection machine learning models 452, e.g., by referring to the corresponding portions of the cardiac EGM.

Figure 6:
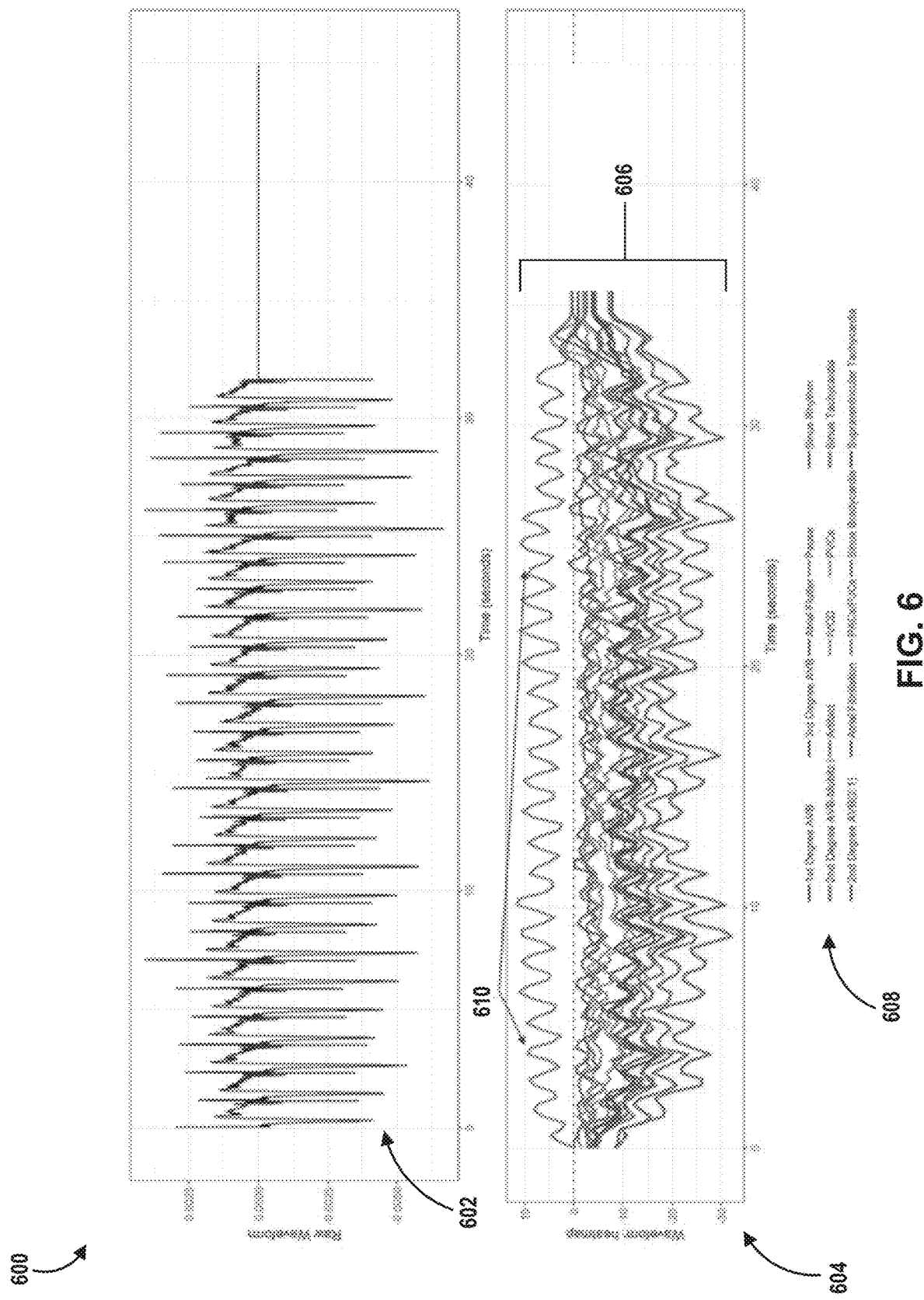
FIG. 6 is a diagram illustrating an example episode review screen including a visualization of the likelihood of each of a plurality of arrhythmia classifications over time during an episode.
Figure 7:
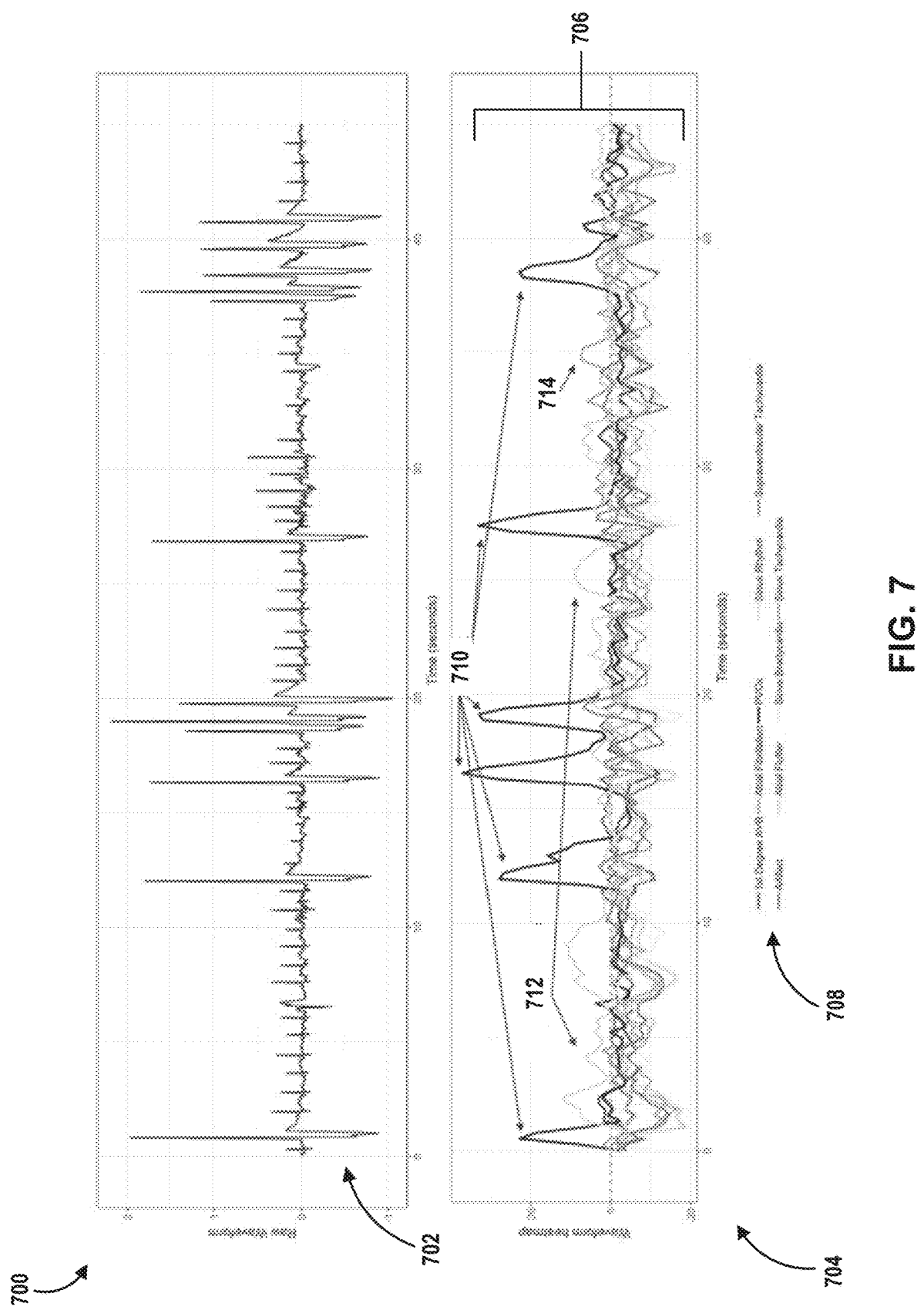
FIG. 7 is a diagram illustrating another example episode review screen including a visualization of the likelihood of each of a plurality of arrhythmia classifications over time during an episode.

FIGS. 6 and 7 are diagrams illustrating example episode review screens 600, 700 including a visualization of the likelihood of each of a plurality of arrhythmia classifications over time during an episode. Each of screens 600 and 700 display a respective cardiac EGM 602, 702 in conjunction with a respective graph 604, 704 of arrhythmia type classification activation data. Each of graphs 604 and 704 includes a respective set of plots 606, 706, and a respective key 608, 708. Each of plots 606 and 706 is a plot of likelihood values over time for a respective arrhythmia type classification. Keys 608 and 708 identify the arrhythmia type classification for each of the plots.

Graph 604 further includes an annotation 610 identifying areas of graph 604 where the plot 606 associated with one of the arrhythmia type classifications, e.g., bradycardia, has relatively higher likelihood values associated with the classification of the associated episode as having at least one arrhythmia of that type. Similarly, graph 704 includes annotations 710, 712, and 714, each of which indicates areas of graph 704 where the respective plot 606 associated with one of the arrhythmia type classifications, e.g., PVCs, atrial fibrillation, and sinus tachycardia, has relatively higher likelihood values associated with the classification of the associated episode as having at least one arrhythmia of that type. By displaying cardiac EGMs 602, 702, graphs 604, 704, and annotations 610, 710, 712, and 714 in conjunction on screens 600, 700, monitoring system 450 may allow a user to more readily review, understand, and confirm (or reject) the arrhythmia detections and classifications made by monitoring system 450 for the episode.

By displaying cardiac EGMs 602, 702, graphs 604, 704, and annotations 610, 710, 712, and 714 in conjunction on screens 600, 700, monitoring system 450 may allow a user to quickly identify portions of the cardiac EGMs on which to focus when reviewing the episode to identify/confirm arrhythmia presence or absence. In some examples, monitoring system 450 may also use the activation data to automate identification of segments of episode data from one episode, e.g., segments of the cardiac EGM, to include in a report to be reviewed by a user. In some cases, episodes are of extended durations (e.g., 1 minute) and might contain multiple arrhythmias at different times during the episode. While reports generated from such episodes may include a presentation of the entire cardiac EGM stored for the episode, such reports may additionally or alternatively include representative segments, where each segment may include a plurality of consecutive seconds of cardiac EGM data.

Monitoring system 450 may identify one or more times (in the episode duration) at which the activation data for a particular arrhythmia type is highest and/or exceeds a threshold. Monitoring system 450 may select, based on the identified times, segments of the cardiac EGM to present to a user as being representative of the reason for detection of that arrhythmia type. For example, with reference to FIG. 7, the highest likelihood value for the PVC class activation map occurs at the spike at about 18 seconds from the start of the episode. Monitoring system 450 may present a six second segment of the cardiac EGM 15 seconds to 21 seconds, e.g., if there is a requirement to report a representative PVC segment for this episode.

Figure 8:
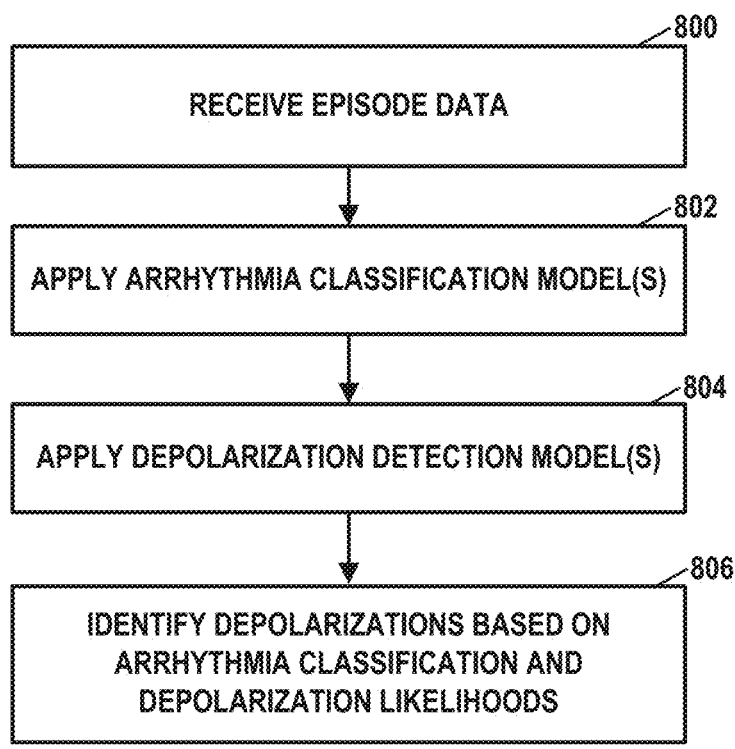
FIG. 8 is a flow diagram illustrating example operation for identifying depolarizations during an episode based on both arrhythmia classification and depolarization likelihoods.

FIG. 8 is a flow diagram illustrating example operation for identifying depolarizations during an episode based on both arrhythmia classification and depolarization likelihoods. According to the example illustrated by FIG. 8, monitoring system 450 receives episode data recorded by IMD 10 for an episode (800). The episode is associated with a period of time, and the episode data comprises a cardiac EGM sensed by IMD 10 during the period of time. The episode data may include other signals sensed by IMD 10 during the period of time, or data derived from the cardiac EGM or other signal.

Monitoring system 450 applies one or more arrhythmia classification machine learning models 452 to the episode data, e.g., to the cardiac EGM data (802). Monitoring system 450 may also derive, for each arrhythmia type classification, class activation data indicating varying likelihoods of the classification over the period of time. Monitoring system 450 also applies one or more depolarization detection machine learning models 454 to the episode data, the one or more depolarization detection machine learning models 454 configured to output a set of depolarization likelihood values, each of the depolarization likelihood values of the set representing the likelihood that a depolarization occurred at a respective time during the period of time (804). Monitoring system 450 identifies one or more depolarizations during the episode based on the arrhythmia type likelihood values and depolarization likelihood values (806).

Monitoring system 450 may use the arrhythmia type likelihood values to identify depolarizations in a variety of ways. For example, monitoring system may apply the time series arrhythmia type likelihood values, e.g., the activation data, such as illustrated by the activation data plots 606 and 706 illustrated in FIG. 7, as inputs to the one or more depolarization detection machine learning models 454 along with the episode data, e.g., cardiac EGM data. The one or more depolarization detection machine learning models 454 may be trained to determine the likelihoods of depolarizations at a given time of the episode based on both the cardiac EGM input and the likelihood values for one of more arrhythmia type classifications. In some examples, likelihood values for certain arrhythmia type classifications are selected as inputs to the one or more depolarization detection machine learning models 454, rather than all arrhythmia type classifications for which the one or more arrhythmia detection machine learning models 452 output likelihood values.

In some examples, monitoring system 450 may apply heuristic rules to the arrhythmia type classification likelihood values for one or more, e.g., selected, arrhythmia type classifications. Based on the rules and the arrhythmia type classification likelihood values at certain times during the episode, monitoring system 450 may modify, e.g., increase or decrease, the depolarization likelihood values provided by the one or more depolarization detection models 454 at certain times during the episode. Additionally or alternatively, monitoring system 450 may, based on the rules and the arrhythmia type classification likelihood values at certain times during the episode, similarly modify the depolarization likelihood threshold to which monitoring system compares depolarization likelihood values from certain times during the episode. The modification of the depolarization likelihood values and/or depolarization likelihood threshold may, in either case, result in detection of a depolarization by monitoring system 450 that would not have otherwise been detected. The heuristic rules may be configured for modification of the depolarization likelihood values and/or depolarization likelihood threshold at the time or a particular time subsequent to the time of a relatively high likelihood of an arrhythmia of a certain type based on an understanding of the timing of depolarizations during an arrhythmia of that type. For example, the heuristic rules may be configured for modification of the depolarization likelihood values and/or depolarization likelihood threshold a particular time subsequent to the time of a relatively high likelihood of a tachyarrhythmia based a typical depolarization rate or inter-depolarization interval for the tachyarrhythmia.

Figure 9:
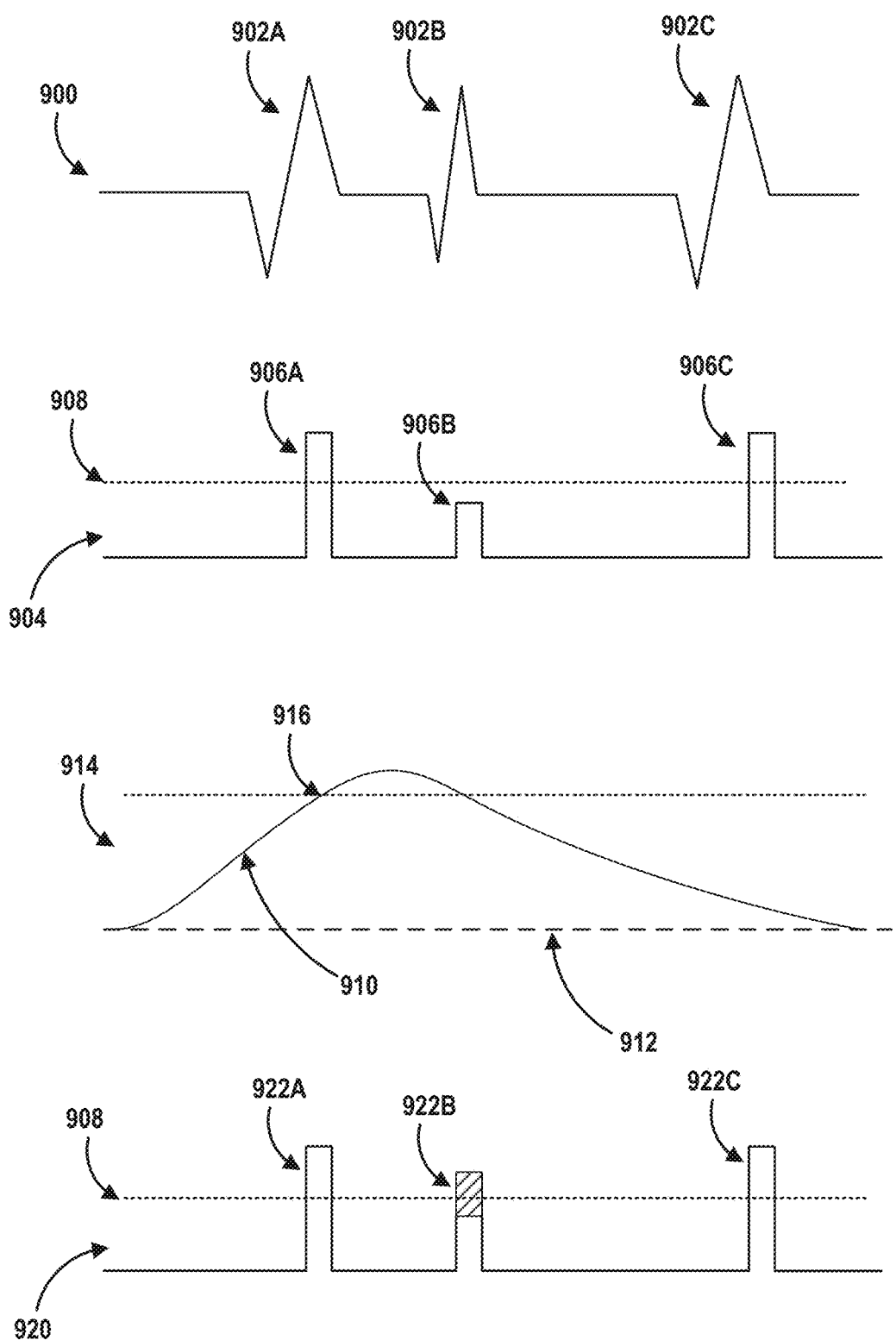
FIG. 9 is a conceptual diagram illustrating example techniques for identifying depolarizations during an episode based on both arrhythmia classification and depolarization likelihoods.

FIG. 9 is a conceptual diagram illustrating example techniques for identifying depolarizations during an episode based on both arrhythmia classification and depolarization likelihoods. In particular, FIG. 9 illustrates a cardiac electrogram 900 including depolarizations 902A-902C (collectively, "depolarizations 902"). FIG. 9 also illustrates a depolarization likelihood value plot 904. Depolarization likelihood value plot 904 includes regions 906A-906C (collectively, "regions 906") having relatively higher depolarization likelihood values, and which correspond in time to depolarizations 902. A depolarization likelihood threshold 908 is also illustrated. The depolarization likelihood values of plot 904 at region 906B do not exceed depolarization likelihood threshold 908. Consequently, monitoring system 450 would not detect depolarization 902B.

FIG. 9 also illustrates a plot of arrhythmia classification likelihood values 910 for a tachyarrhythmia relative to a baseline 912 and a threshold 914. Threshold 914 may be established by the heuristic rules applied by monitoring system 450. As illustrated in FIG. 9, arrhythmia classification likelihood values 910 exceed threshold 914 at time 916.

FIG. 9 also illustrates a depolarization likelihood value plot 920 including regions 922A-922C (collectively, "regions 922") having relatively higher depolarization likelihood values, and which correspond in time to depolarizations 902. Regions 922A and 922C are the same as regions 906A and 906C, i.e., have not been modified by monitoring system 450 based on the arrhythmia classification likelihood values 910 and heuristic rules. However, based on the arrhythmia classification likelihood values 910 and heuristic rules, monitoring system 450 has increased region 922B relative to region 906B based on arrhythmia classification likelihood values 910 having exceed threshold 908. Consequently, monitoring system 450 may detect depolarization 902B.

In addition to using the depolarization and arrhythmia likelihood data to identify depolarizations within an episode using the techniques described herein, e.g., with respect to FIGS. 8 and 9, monitoring system 450 may use the depolarization and arrhythmia likelihood data to determine a type of depolarization for depolarizations within the episode. Types of depolarizations may include, as examples, normal, premature ventricular contraction, premature atrial contraction, and artifact/noise. The one or more arrhythmia classification machine learning models 452 used by monitoring system to classify the episode may be configured to classify the episode as, among other classifications, premature ventricular contraction, premature atrial contraction, and artifact/noise. Consequently, monitoring system 450 may be configured to derive class activation values over time for premature ventricular contraction, premature atrial contraction, and artifact/noise as classifications. Monitoring system 450 may further determine which of a plurality types, e.g., normal, premature ventricular contraction, premature atrial contraction, and artifact/noise, the depolarizations using the class activation data for those arrhythmia types.

In some examples, monitoring system 450 may label depolarizations occurring when the likelihood values for the noise/artifact classification meet (e.g., exceed) the threshold as artifact/noise. Monitoring system 450 may consider inter-depolarization intervals for the remaining (e.g., non-artifact/noise) depolarizations during the episode, and determine whether any of these remaining depolarizations are "premature" based on their inter-depolarization intervals (e.g., R-R intervals) meeting (e.g., being less than) a threshold. The inter-depolarization interval threshold may be determined based on a mean or median of inter-depolarization intervals during the episode, e.g., the threshold may be a fraction or percentage of the mean or median inter-depolarization interval during the episode. Monitoring system 450 may label a premature depolarization as a premature ventricular contraction or a premature atrial contraction based on the likelihood values corresponding in time to the premature depolarization meeting (e.g., exceeds) a threshold. Monitoring system 450 may label depolarizations identified during the episode, but not determined to be one of premature ventricular contraction, premature atrial contraction, or artifact/noise, as normal.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1

A computer-implemented method comprising: receiving, by processing circuitry of a medical device system, episode data for an episode stored by a medical device of a patient, wherein the episode is associated with a period of time, and the episode data comprises a cardiac electrogram sensed by the medical device during the period of time; applying, by the processing circuitry, one or more machine learning models to the episode data, the one or more machine learning models configured to output a respective likelihood value for each of a plurality of arrhythmia type classifications, each of the likelihood values representing a likelihood that the respective arrhythmia type classification occurred at any point during the period of time; based on the application of the one or more machine learning models to the episode data, deriving, by the processing circuitry and for each of the arrhythmia type classifications, class activation data indicating varying likelihoods of the classification over the period of time; and displaying, by the processing circuitry and to a user, a graph of the varying likelihoods of the arrhythmia type classifications over the period of time.

Example 2

The method of example 1, wherein displaying the graph comprises displaying the graph in conjunction with the cardiac electrogram.

Example 3

The method of example 1 or 2, further comprising indicating on the graph, by the processing circuitry, at least one time of higher likelihood for at least one of the arrhythmia type classifications relative to other times of the graph for the at least one arrhythmia type classification.

Example 4

The method of example 3, further comprising indicating, by the processing circuitry and based on the output of the one or more machine learning models, that the at least one arrhythmia type classification occurred at any point during the period of time, wherein indicating on the graph at least one time of higher likelihood for the at least one arrhythmia type classification comprises indicating on the graph at least one time of higher likelihood for the at least one arrhythmia type classification in response to indicating that the at least one arrhythmia type classification occurred at any point during the period of time.

Example 5

The method of any of examples 1 to 4, wherein the plurality of arrhythmia type classifications includes a plurality of bradycardia, pause, ventricular tachycardia, ventricular fibrillation, supraventricular tachycardia, atrial fibrillation, atrial flutter, sinus tachycardia, premature ventricular contraction, premature atrial contraction, wide complex tachycardia, and atrioventricular block.

Example 6

The method of any of examples 1 to 5, wherein each of the one or more machine learning models comprises a plurality of layers, and wherein deriving the activation data comprises deriving the activation layer from an output of an intermediate layer of the plurality of layers.

Example 7

The method of example 6, wherein the intermediate layer comprises a global average pooling layer.

Example 8

The method of any of examples 1 to 7, further comprising: selecting a segment from the cardiac electrogram based on the class activation data; and displaying the selected segment of the cardiac electrogram.

Example 9

The method of example 8, wherein selecting the segment comprises: identifying a time during the episode based on class activation data for one the arrhythmia type classifications; and selecting a segment of the cardiac electrogram including the identified time.

Example 10

A computer-implemented method comprising: receiving, by processing circuitry of a medical device system, episode data for an episode stored by a medical device of a patient, wherein the episode is associated with a period of time, and the episode data comprises a cardiac electrogram sensed by the medical device during the period of time; applying, by the processing circuitry, one or more arrhythmia classification machine learning models to the episode data, the one or more arrhythmia classification machine learning models configured to output, for each of a plurality of arrhythmia type classifications, a respective set of arrhythmia type likelihood values, each of the arrhythmia type likelihood values of the set representing a likelihood that the respective arrhythmia type classification occurred at a respective time during the period of time; applying, by the processing circuitry, one or more depolarization detection machine learning models to the episode data, the one or more depolarization detection machine learning models configured to output a set of depolarization likelihood values, each of the depolarization likelihood values of the set representing a likelihood that a depolarization occurred at a respective time during the period of time; and identifying, by the processing circuitry, one or more depolarizations during the episode based on the arrhythmia type likelihood values and depolarization likelihood values.

Example 11

The method of example 10, wherein each of the one or more arrhythmia classification machine learning models comprises a plurality of layers, the method further comprising deriving, by the processing circuitry, the sets of arrhythmia type likelihood values from an output of an intermediate layer of the plurality of layers.

Example 12

The method of example 11, wherein the intermediate layer comprises a global average pooling layer.

Example 13

The method of any of examples 10 to 12, wherein applying the one or more depolarization detection machine learning models to the episode data and identifying one or more depolarizations based on the arrhythmia type likelihood values and depolarization likelihood values comprises applying the one or more depolarization detection machine learning models to the episode data and the arrhythmia type likelihood values.

Example 14

The method of any of examples 10 to 13, wherein identifying one or more depolarizations based on the arrhythmia type likelihood values and depolarization likelihood values comprises: modifying one or more of the depolarization likelihood values based on one or more of the arrhythmia type likelihood values; and identifying the one or more depolarizations based on the one or more modified depolarization likelihood values.

Example 15

The method of any of examples 10 to 14, wherein identifying one or more depolarizations based on the arrhythmia type likelihood values and depolarization likelihood values comprises: modifying a depolarization likelihood threshold based on one or more of the arrhythmia type likelihood values; comparing the depolarization likelihood values to the modified depolarization likelihood threshold; and identifying the one or more depolarizations based on the comparison.

Example 16

The method of any of examples 10 to 15, wherein the depolarizations comprise at least one of R-waves or QRS complexes.

Example 17

The method of any of examples 10 to 16, further comprising labeling each of the one or more identified depolarizations as one of a plurality of depolarization types based on the arrhythmia type likelihood values.

Example 18

The method of example 17, wherein the plurality of depolarization types include a plurality of normal, premature ventricular contraction, premature atrial contraction, noise, or artifact.

Example 19

A medical device system comprising a medical device configured to: sense a cardiac electrogram of a patient via a plurality of electrodes; and store episode data for an episode, wherein the episode is associated with a period of time, and the episode data comprises the cardiac electrogram sensed by the medical device during the period of time. The medical device system further comprises processing circuitry configured to perform the methods of any of examples 1 to 18.

Example 20

The medical device system of example 19, wherein the processing circuitry comprises processing circuitry of a computing device.

Example 21

The medical device system of example 19 or 20, wherein the medical device is implantable.

Example 22

A non-transitory computer-readable medium comprising instructions that, when executed by processing circuitry of a computing system, cause the computing system to perform the method of any of examples 1 to 18.

Various examples have been described. These and other examples are within the scope of the following claims.

What is claimed is:

1. A computer-implemented method for operating processing circuitry of a medical device system that includes a medical device of a patient, the method comprising:
   receiving, by the processing circuitry, episode data for an episode stored by the medical device, wherein the episode is associated with a period of time, and the episode data comprises a cardiac electrogram sensed by the medical device during the period of time;
   applying, by the processing circuitry, one or more arrhythmia classification machine learning models to the episode data, the one or more arrhythmia classification machine learning models configured to output a respective arrhythmia type likelihood value for each of a plurality of arrhythmia type classifications, each of the arrhythmia type likelihood values representing a likelihood that the respective arrhythmia type classification occurred at any point during the period of time;
   applying, by the processing circuitry, one or more depolarization detection machine learning models to the episode data, the one or more depolarization detection machine learning models configured to output a set of depolarization likelihood values, each of the depolarization likelihood values of the set representing a likelihood that a depolarization occurred at a respective time during the period of time;
   identifying, by the processing circuitry, one or more depolarizations during the episode based on the arrhythmia type likelihood values and depolarization likelihood values; and
   displaying, by the processing circuitry and to a user, at least one of the arrhythmia type likelihood values and an indication of the one or more identified depolarizations over the period of time.

2. The method of claim 1, wherein displaying the at least one of the arrhythmia type likelihood values and the indication of the one or more identified depolarizations comprises displaying the at least one of the arrhythmia type likelihood values and the indication of the one or more identified depolarizations in conjunction with the cardiac electrogram.

3. The method of claim 1, further comprising:
   based on the applying of the one or more arrhythmia classification machine learning models to the episode data, deriving, by the processing circuitry and for each of the arrhythmia type classifications, class activation data indicating varying likelihoods of the classification over the period of time;
   displaying, by the processing circuitry and to the user, a graph of the varying likelihoods for at least one of the arrhythmia type classifications; and
   indicating on the graph, by the processing circuitry, at least one time of higher likelihood for the at least one arrhythmia type classification relative to other times of the graph for the at least one arrhythmia type classification.

4. The method of claim 3, further comprising indicating, by the processing circuitry and based on the output of the one or more arrhythmia classification machine learning models, that the at least one arrhythmia type classification occurred at any point during the period of time,
   wherein indicating on the graph at least one time of higher likelihood for the at least one arrhythmia type classification comprises indicating on the graph, by the processing circuitry, the at least one time of higher likelihood for the at least one arrhythmia type classification in response to indicating that the at least one arrhythmia type classification occurred at any point during the period of time.

5. The method of claim 3, wherein each of the one or more arrhythmia classification machine learning models comprises a plurality of layers, and wherein deriving the class activation data comprises deriving the class activation data from an output of an intermediate layer of the plurality of layers.

6. The method of claim 5, wherein the intermediate layer comprises a global average pooling layer.

7. The method of claim 1, wherein the plurality of arrhythmia type classifications includes a plurality of: bradycardia, pause, ventricular tachycardia, ventricular fibrillation, supraventricular tachycardia, atrial fibrillation, atrial flutter, sinus tachycardia, premature ventricular contraction, premature atrial contraction, wide complex tachycardia, and atrioventricular block.

8. The method of claim 1, wherein applying the one or more depolarization detection machine learning models to the episode data and identifying one or more depolarizations based on the arrhythmia type likelihood values and depolarization likelihood values comprises applying the one or more depolarization detection machine learning models to the episode data and the arrhythmia type likelihood values.

9. The method of claim 1, wherein identifying one or more depolarizations based on the arrhythmia type likelihood values and depolarization likelihood values comprises at least one of:
modifying one or more of the depolarization likelihood values based on one or more of the arrhythmia type likelihood values; or
modifying a depolarization likelihood threshold based on one or more of the arrhythmia type likelihood values.

10. The method of claim 1, further comprising labeling each of the one or more identified depolarizations as one of a plurality of depolarization types based on the arrhythmia type likelihood values, wherein the plurality of depolarization types include a plurality of normal, premature ventricular contraction, premature atrial contraction, noise, or artifact.

11. A medical device system comprising:
a medical device configured to:
sense a cardiac electrogram of a patient via a plurality of electrodes; and
store episode data for an episode, wherein the episode is associated with a period of time, and the episode data comprises the cardiac electrogram sensed by the medical device during the period of time; and
processing circuitry configured to:
receive the episode data;
apply one or more arrhythmia classification machine learning models to the episode data, the one or more arrhythmia classification machine learning models configured to output a respective arrhythmia type likelihood value for each of a plurality of arrhythmia type classifications, each of the arrhythmia type likelihood values representing a likelihood that the respective arrhythmia type classification occurred at any point during the period of time;
apply one or more depolarization detection machine learning models to the episode data, the one or more depolarization detection machine learning models configured to output a set of depolarization likelihood values, each of the depolarization likelihood values of the set representing a likelihood that a depolarization occurred at a respective time during the period of time;
identify one or more depolarizations during the episode based on the arrhythmia type likelihood values and depolarization likelihood values; and
display, to a user, at least one of the arrhythmia type likelihood values and an indication of the one or more identified depolarizations over the period of time.

12. The medical device system of claim 11, wherein the processing circuitry is configured to display the at least one of the arrhythmia type likelihood values and the indication of the one or more identified depolarizations comprises displaying the at least one of the arrhythmia type likelihood values and the indication of the one or more identified depolarizations in conjunction with the cardiac electrogram.

13. The medical device system of claim 11, wherein the processing circuitry is configured to:
based on the application of the one or more arrhythmia classification machine learning models to the episode data, derive, for each of the arrhythmia type classifications, class activation data indicating varying likelihoods of the classification over the period of time;
display, to the user, a graph of the varying likelihoods for at least one of the arrhythmia type classifications; and
indicate on the graph, by the processing circuitry, at least one time of higher likelihood for the at least one arrhythmia type classification relative to other times of the graph for the at least one arrhythmia type classification.

14. The medical device system of claim 13, wherein the processing circuitry is configured to:
indicate, based on the output of the one or more arrhythmia classification machine learning models, that the at least one arrhythmia type classification occurred at any point during the period of time; and
indicate on the graph the at least one time of higher likelihood for the at least one arrhythmia type classification in response to indicating that the at least one arrhythmia type classification occurred at any point during the period of time.

15. The medical device system of claim 11, wherein the plurality of arrhythmia type classifications includes a plurality of bradycardia, pause, ventricular tachycardia, ventricular fibrillation, supraventricular tachycardia, atrial fibrillation, atrial flutter, sinus tachycardia, premature ventricular contraction, premature atrial contraction, wide complex tachycardia, and atrioventricular block.

16. The medical device system of claim 11, wherein each of the one or more arrhythmia classification machine learning models comprises a plurality of layers, and wherein deriving the class activation data comprises deriving the class activation data from an output of an intermediate layer of the plurality of layers.

17. The medical device system of claim 16, wherein the intermediate layer comprises a global average pooling layer.

18. The medical device system of claim 11, wherein, to identify the one or more depolarizations based on the arrhythmia type likelihood values and depolarization likelihood values, the processing circuitry is configured to apply the one or more depolarization detection machine learning models to the episode data and the arrhythmia type likelihood values.

19. The medical device system of claim 11, wherein, to identify the one or more depolarizations based on the arrhythmia type likelihood values and depolarization likelihood values, the processing circuitry is configured to at least one of:

modify one or more of the depolarization likelihood values based on one or more of the arrhythmia type likelihood values; or modify a depolarization likelihood threshold based on one or more of the arrhythmia type likelihood values.

20. The medical device system of claim 11, wherein the processing circuitry is configured to label each of the one or more identified depolarizations as one of a plurality of depolarization types based on the arrhythmia type likelihood values, wherein the plurality of depolarization types include a plurality of normal, premature ventricular contraction, premature atrial contraction, noise, or artifact.

21. The medical device system of claim 11, wherein the processing circuitry comprises processing circuitry of a computing device.

22. The medical device system of claim 11, wherein the medical device is implantable.

23. A non-transitory computer-readable medium comprising instructions that, when executed by processing circuitry of a computing system, cause the computing system to:

receive episode data for an episode stored by a medical device of a patient, wherein the episode is associated with a period of time, and the episode data comprises a cardiac electrogram sensed by the medical device during the period of time;

apply one or more arrhythmia classification machine learning models to the episode data, the one or more arrhythmia classification machine learning models configured to output a respective arrhythmia type likelihood value for each of a plurality of arrhythmia type classifications, each of the arrhythmia type likelihood values representing a likelihood that the respective arrhythmia type classification occurred at any point during the period of time;

apply one or more depolarization detection machine learning models to the episode data, the one or more depolarization detection machine learning models configured to output a set of depolarization likelihood values, each of the depolarization likelihood values of the set representing a likelihood that a depolarization occurred at a respective time during the period of time;

identify one or more depolarizations during the episode based on the arrhythmia type likelihood values and depolarization likelihood values; and display at least one of the arrhythmia type likelihood values and an indication of the one or more identified depolarizations over the period of time.

\* \* \* \* \*